United States Patent
Sugimoto

(10) Patent No.: US 10,717,690 B2
(45) Date of Patent: Jul. 21, 2020

(54) METHOD OF MANUFACTURING OCTAFLUOROCYCLOPENTENE

(71) Applicant: ZEON CORPORATION, Chiyoda-ku Tokyo (JP)

(72) Inventor: Tatsuya Sugimoto, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 16/612,760

(22) PCT Filed: Jun. 1, 2018

(86) PCT No.: PCT/JP2018/021232
§ 371 (c)(1),
(2) Date: Nov. 12, 2019

(87) PCT Pub. No.: WO2018/235566
PCT Pub. Date: Dec. 27, 2018

(65) Prior Publication Data
US 2020/0199050 A1 Jun. 25, 2020

(30) Foreign Application Priority Data
Jun. 22, 2017 (JP) .................................. 2017-122362

(51) Int. Cl.
*C07C 17/20* (2006.01)
*C07C 23/08* (2006.01)
(52) U.S. Cl.
CPC .............. *C07C 17/20* (2013.01); *C07C 23/08* (2013.01)
(58) Field of Classification Search
CPC ................................ C07C 17/20; C07C 23/08
See application file for complete search history.

(56) References Cited

U.S. PATENT DOCUMENTS

| | | | |
|---|---|---|---|
| 3,567,788 A | 3/1971 | Carr et al. | |
| 6,211,420 B1 | 4/2001 | Sekiya et al. | |

FOREIGN PATENT DOCUMENTS

| | | |
|---|---|---|
| JP | H0995458 A | 4/1997 |
| JP | 2001240568 A | 9/2001 |
| JP | 2001247493 A | 9/2001 |
| JP | 2001261594 A | 9/2001 |
| JP | 2006151998 A | 6/2006 |
| WO | 9743233 A1 | 11/1997 |

OTHER PUBLICATIONS

John T. Maynard, The Synthesis of Highly Fluorinated Compounds by Use of Potassium Fluoride in Polar Solvents, The Journal of Organic Chemistry, Jan. 1, 1963, pp. 112-115, vol. 28.
Dec. 24, 2019, International Preliminary Report on Patentability issued in the International Patent Application No. PCT/JP2018/021232.

*Primary Examiner* — Jafar F Parsa
(74) *Attorney, Agent, or Firm* — Kenja IP Law PC

(57) ABSTRACT

Provided is a method of manufacturing octafluorocyclopentene by bringing 1-chloroheptafluorocyclopentene into contact with an alkali metal fluoride. The manufacturing method includes a feedstock heating step of heating 1-chloroheptafluorocyclopentene to not lower than 40° C. and not higher than 55° C. and a fluorination step of maintaining a suspension containing a polar aprotic solvent and an alkali metal fluoride at 85° C. or higher while supplying heated 1-chloroheptafluorocyclopentene into the suspension and performing fluorination thereof to obtain octafluorocyclopentene.

3 Claims, No Drawings

METHOD OF MANUFACTURING OCTAFLUOROCYCLOPENTENE

TECHNICAL FIELD

The present disclosure relates to a method of manufacturing octafluorocyclopentene. In particular, the present disclosure relates to a manufacturing method in which 1,2,3,3,4,4,5,5-octafluorocyclopentene is manufactured through fluorination of 1-chloroheptafluorocyclopentene.

BACKGROUND 1,2,3,3,4,4,5,5-Octafluorocyclopentene (hereinafter, also referred to as "octafluorocyclopentene") is useful as a gas for plasma reaction in etching, chemical vapor deposition (CVD), and so forth that may be performed in a manufacturing step of a semiconductor device or as a feedstock for a fluorine-containing pharmaceutical intermediate, a photochromic molecule material, or the like. Highly purified octafluorocyclopentene, in particular, can suitably be used as a plasma etching gas, CVD gas, or the like that can be used in a manufacturing step of a semiconductor device.

A number of methods of manufacturing octafluorocyclopentene have been proposed in recent years. For example, Patent Literature (PTL) 1 discloses that octafluorocyclopentene was obtained in a yield of 93.1% by using potassium fluoride to perform fluorination in N,N-dimethylformamide solvent with respect to a mixture of compounds including at least two chlorine atoms that was obtained through fluorination of hexachlorocyclopentadiene by anhydrous hydrogen fluoride. This mixture contained 1,2-dichlorohexafluorocyclopentene, 1,2,3-trichloroheptafluorocyclopentene, and 1,2,3,5-tetrachlorotetrafluorocyclopentene.

PTL 2 discloses that octafluorocyclopentene was obtained in a yield of 87.8% using 1,2-dichlorohexafluorocyclopentene as a feedstock by carrying out a reaction in N,N-dimethylformamide solvent using potassium fluoride as a fluorinating agent while adjusting the dripping rate of the feedstock and the withdrawal rate of octafluorocyclopentene (product).

PTL 3 discloses that octafluorocyclopentene was obtained in a yield of 90% by using potassium fluoride to perform fluorination of a mixture containing 1-chloroheptafluorocyclopentene, 1,2-di chlorohexafluorocyclopentene, trichloropentafluorocyclopentene, tetrachlorotetrafluorocyclopentene, and pentachlorotrifluorocyclopentene that was obtained through gas phase fluorination by anhydrous hydrogen fluoride using octachlorocyclopentene as a starting material.

PTL 4 discloses that octafluorocyclopentene was obtained in a yield of 87% by using potassium fluoride to fluorinate a feedstock having 1-chloroheptafluorocyclopentene as a main component in N,N-dimethylformamide solvent.

PTL 5 discloses that octafluorocyclopentene was obtained in a yield of 72% using 1-chloroheptafluorocyclopentene as a feedstock by performing heating under reflux in a mixed solvent of N,N-dimethylformamide and benzene, which is a non-polar solvent, with potassium fluoride as a fluorinating agent.

Non-Patent Literature (NPL) 1 discloses that octafluorocyclopentene was obtained in a yield of 72% using octachlorocyclopentene as a feedstock by performing fluorination in N-methylpyrrolidone solvent with potassium fluoride as a fluorinating agent.

CITATION LIST

Patent Literature

PTL 1: WO 1997/043233 A1
PTL 2: JP H9-95458 A
PTL 3: JP 2006-151998 A
PTL 4: JP 2001-247493 A
PTL 5: U.S. Pat. No. 3,567,788 A

Non-Patent Literature

NPL 1: John T. Maynard, Journal of Organic Chemistry, 1963, vol. 28, p. 112-115

SUMMARY

Technical Problem

With regards to methods of manufacturing octafluorocyclopentene that can suitably be used in applications such as described above, there has been increasing need for higher yield in recent years. However, it has not been possible to sufficiently increase the yield of octafluorocyclopentene in various manufacturing methods that have previously been proposed, such as those described above.

Accordingly, an objective of the present disclosure is to provide a manufacturing method that can sufficiently increase the yield of octafluorocyclopentene.

Solution to Problem

In view of the above, the inventor firstly focused on a fluorination step in which 1-chloroheptafluorocyclopentene is brought into contact with an alkali metal fluoride in order to fluorinate the 1-chloroheptafluorocyclopentene. More specifically, the inventor attempted to carry out this fluorination step by supplying a feedstock of 1-chloroheptafluorocyclopentene into a reactor while reacting the 1-chloroheptafluorocyclopentene with an alkali metal fluoride serving as a fluorinating agent and removing the obtained octafluorocyclopentene from the reactor in accordance with a method described in PTL 2 or PTL 3. As a result, the inventor found that when 1-chloroheptafluorocyclopentene is continuously supplied into the reactor as a feedstock, the temperature of the inside of the reactor (reaction contents) tends to gradually decrease. In more detail, the inventor determined that the rate of conversion of carbon-chlorine bonds to carbon-fluorine bonds slows significantly when the internal temperature drops below approximately 85° C., and that this leads to reduction of the yield of octafluorocyclopentene, which is the target product.

The inventor presumed that one factor causing the temperature in the reaction of 1-chloroheptafluorocyclopentene and the alkali metal fluoride inside the reaction vessel (i.e., the internal temperature) to decrease is the fact that 1-chloroheptafluorocyclopentene has a low boiling point of 56° C. Note that 1,2-dichlorohexafluorocyclopentene used as a feedstock in PTL 1 and 2, for example, has a boiling point of 90° C., whereas compounds having more chlorine atoms than 1,2-dichlorohexafluorocyclopentene have a boiling point of even higher than 90° C. Also note that a mixture containing two or more of such compounds also has a boiling point of higher than 90° C. Therefore, when a fluorination step carried out in a liquid phase such as disclosed in PTL 1 and 2 is envisaged, it is thought that in a case in which a feedstock of 1-chloroheptafluorocyclopentene is brought into contact with a suspension of a reaction solvent and an alkali metal fluoride, the influence of heat of vaporization and the like will be large and the effect of lowering the internal temperature will be large compared to a case in which 1,2-dichlorohexafluorocyclopentene is used as a feedstock, as in a conventional method. As previously described, if the internal temperature decreases, the rate of the fluorination reaction in the fluorination step slows significantly, and this leads to a large amount of unreacted 1-chloroheptafluorocyclopentene remaining in the reaction system and thus tending to be removed from the reactor together with octafluorocyclopentene, which is the target product. As a consequence, the yield of octafluorocyclopentene may decrease.

One strategy that may be considered for inhibiting reduction of the rate of the fluorination reaction caused by reduction of internal temperature is to slow the rate at which 1-chloroheptafluorocyclopentene is supplied into the reactor as a feedstock. However, this is not a realistic strategy because slowing the feedstock supply rate significantly increases the time required for the fluorination step, which may lead to lower productivity.

Another strategy would be to raise an initial setting for the internal temperature. However, it is expected that when 1-chloroheptafluorocyclopentene is supplied into the reactor as a feedstock, the internal temperature will still decrease due to the low boiling point of 1-chloroheptafluorocyclopentene as previously described, and thus the yield of octafluorocyclopentene will decrease.

Yet another strategy would be to adjust the internal temperature through heating of the reactor during the fluorination step. However, this strategy is unrealistic because it is extremely difficult to perform control such that the heating temperature of the reactor is adjusted in accordance with variation of the internal temperature in order that the internal temperature is constantly at a desired value.

In light of the circumstances set forth above, the inventor reached a new discovery that reduction of internal temperature can be effectively inhibited by supplying 1-chloroheptafluorocyclopentene into the reaction system as a feedstock after the 1-chloroheptafluorocyclopentene has been heated, and in this manner completed the present disclosure.

The present disclosure aims to advantageously solve the problems set forth above by disclosing a method of manufacturing octafluorocyclopentene by bringing 1-choroheptafluorocyclopentene into contact with an alkali metal fluoride to obtain octafluorocyclopentene, comprising: a feedstock heating step of heating 1-chloroheptafluorocyclopentene to not lower than 40° C. and not higher than 55° C.; a fluorination step of maintaining a suspension containing a polar aprotic solvent and the alkali metal fluoride at 85° C. or higher while supplying heated 1-chloroheptafluoropentene into the suspension and performing fluorination thereof to obtain octafluorocyclopentene; and a recovery step of recovering the octafluorocyclopentene that is produced in the fluorination step. This manufacturing method can sufficiently increase the yield of octafluorocyclopentene.

In the presently disclosed method of manufacturing octafluorocyclopentene, the polar aprotic solvent is preferably N,N-dimethylformamide or N,N-dimethylacetamide. When the polar aprotic solvent is N,N-dimethylformamide or N,N-dimethylacetamide, the yield of octafluorocyclopentene can be further increased.

In the presently disclosed method of manufacturing octafluorocyclopentene, the alkali metal fluoride is preferably potassium fluoride or cesium fluoride. When the alkali metal fluoride is potassium fluoride or cesium fluoride, the manufacturing efficiency and yield of octafluorocyclopentene can be further increased.

DETAILED DESCRIPTION

The following provides a detailed description of embodiments of the present disclosure. The presently disclosed method of manufacturing octafluorocyclopentene (hereinafter, also referred to simply as the "presently disclosed manufacturing method", etc.) can suitably be implemented without any specific limitations in a manufacturing apparatus that includes a reactor and a distillation column or a rectification column.

The presently disclosed manufacturing method includes: a feedstock heating step of heating 1-chloroheptafluorocyclopentene to not lower than 40° C. and not higher than 55° C.; a fluorination step of maintaining a suspension containing a polar aprotic solvent and an alkali metal fluoride at 85° C. or higher while supplying heated 1-chloroheptafluoropentene into the suspension and performing fluorination thereof to obtain octafluorocyclopentene; and a recovery step of recovering the octafluorocyclopentene that is produced in the fluorination step. The presently disclosed manufacturing method enables the manufacture of octafluorocyclopentene in a high yield as a result of a feedstock that has been heated to within the specific temperature range set forth above in the feedstock heating step being supplied into the suspension and as a result of the suspension being maintained at a temperature of 85° C. or higher in the fluorination step.

The following provides a detailed description of various elements such as a feedstock, a solvent, and an alkali metal fluoride that can be used in the presently disclosed manufacturing method and then describes an example of various steps that can be included in the presently disclosed manufacturing method.

[Feedstock]

In the presently disclosed manufacturing method, 1-chloroheptafluorocyclopentene is used as a feedstock. The 1-chloroheptafluorocyclopentene may be prepared according to a known method. For example, U.S. Pat. No. 3,567,788 A discloses that 1-chloroheptafluorocyclopentene was obtained in a yield of 74% by fluorinating 1,2-dichlorohexafluorocyclopentene in dimethyl sulfoxide solvent using anhydrous potassium fluoride. Moreover, J P 2001-240568 A discloses that 1-chloroheptafluorocyclopentene was obtained in a maximum yield of 89.1% by using potassium fluoride to fluorinate a feedstock of polychlorofluorocyclopentene (1,2-dichlorohexafluorocyclopentene, 1,2,3-trichloropentafluorocyclopentene, 1,2,4-trichloropentafluorocyclopentene, 1,2,3,4-tetrachlorotetrafluorocyclopentene, 1,2,3,3,4-pentachlorotrifluorocyclopentene, etc.) in a mixed solvent of N,N-dimethylformamide and an aromatic hydrocarbon such as toluene. Furthermore, JP 2001-261594 A discloses that 1-chloroheptafluorocyclopentene was obtained in a maximum yield of 95.6% using 1,1-dichlorooctafluorocyclopentane as a feedstock by performing hydrogen reduction in the presence of a palladium alloy catalyst having a transition metal such as copper, tin, or bismuth as a main component.

[Solvent]

Solvent used in the presently disclosed manufacturing method includes a polar aprotic solvent. It should be noted that the solvent may further include other solvents so long as the effects of the presently disclosed manufacturing method are not impaired.

—Polar Aprotic Solvent—

Amide solvents can suitably be used as the polar aprotic solvent. Examples of amide solvents that can be used include, but are not specifically limited to, N-methylformamide (boiling point: 197° C.), N,N-dimethylformamide (boiling point: 153° C.), N,N-diethylformamide (boiling point: 177° C.), acetamide (boiling point: 222° C.), N,N- dimethylacetamide (boiling point: 165° C.), N,N-diethylacetamide (boiling point: 185° C.), N-methylpyrrolidone (boiling point: 202° C.), and N,N-dimethylimidazolidinone (boiling point: 225° C.). Of these amide solvents, linear amide solvents such as N-methylformamide, N,N-dimethylformamide, N,N-diethylformamide, acetamide, N,N-dimethylacetamide, and N,N-diethylacetamide are preferable in view that they can further increase the yield of octafluorocyclopentene, and N,N-dimethylformamide and N,N-dimethylacetamide, the industrial acquisition of which is particularly easy, are more preferable. Note that the "boiling point" of various solvents referred to in the present specification is the boiling point at 1 atmosphere.

A glycol ether, which is another polar aprotic solvent, may be mixed and used in a proportion of 30 volume % or less relative to 100 volume % of an amide solvent as the polar aprotic solvent. Note that the "volume proportion" referred to in the present specification is the volume proportion at 23° C. Examples of such glycol ethers that can be used include, but are not specifically limited to, dialkyl ethers of polyethylene glycol and dialkyl ethers of polypropylene glycol. Specific examples of dialkyl ethers of polyethylene glycol that can be used include diethylene glycol dimethyl ether (boiling point: 162° C.), diethylene glycol diethyl ether (boiling point: 188° C.), diethylene glycol ethyl methyl ether (boiling point: 179° C.), diethylene glycol dibutyl ether (boiling point: 255° C.), triethylene glycol dimethyl ether (boiling point: 216° C.), triethylene glycol diethyl ether (boiling point: >216° C.), tetraethylene glycol dimethyl ether (boiling point: 276° C.), and tetraethylene glycol diethyl ether (boiling point: >276° C.). Specific examples of dialkyl ethers of polypropylene glycol that can be used include dipropylene glycol dimethyl ether (boiling point: 175° C.), dipropylene glycol diethyl ether (boiling point: >175° C.), and tripropylene glycol dimethyl ether (boiling point: >241° C.).

The boiling point of the polar aprotic solvent is preferably 140° C. or higher, and is preferably 150° C. or higher. When the boiling point of the polar aprotic solvent is not lower than any of the lower limits set forth above, the yield of octafluorocyclopentene can be more sufficiently increased, and the manufacturing efficiency of octafluorocyclopentene can be increased.

The amount of the polar aprotic solvent that is used per 1 g of 1-chloroheptafluorocyclopentene used as a feedstock is preferably 1.0 mL or more, and more preferably 1.2 mL or more, and is preferably 1.5 mL or less. When the amount of the polar aprotic solvent that is used is not less than any of the lower limits set forth above, the viscosity of the suspension does not increase excessively, ease of stirring increases in stirring for bringing 1-chloroheptafluorocyclopentene and the alkali metal fluoride into contact in the liquid phase during the fluorination step, and the efficiency of contacting thereof is further improved, which enables higher fluorination reaction efficiency in the fluorination step. Moreover, the use of an amount of polar aprotic solvent that is not more than the upper limit set forth above is financially beneficial in industry.

The polar aprotic solvent has preferably undergone a drying process in advance. The drying can be carried out by a standard method without any specific limitations. For example, a method in which a desiccant is added to the used polar aprotic solvent and is left therewith for a certain time and/or a method in which the polar aprotic solvent is passed through a column packed with a desiccant and is recovered may be adopted.

[Alkali Metal Fluoride]

Some of the alkali metal fluoride is dissolved in the polar aprotic solvent and the remaining alkali metal fluoride is dispersed in the polar aprotic solvent so as to form a suspension. The alkali metal fluoride in the suspension functions as a fluorinating agent for the feedstock in the presently disclosed manufacturing method. Examples of alkali metal fluorides that can be used include sodium fluoride, lithium fluoride, rubidium fluoride, potassium fluoride, and cesium fluoride. Of these alkali metal fluorides, potassium fluoride and cesium fluoride are preferable from a viewpoint of increasing the manufacturing efficiency and yield of octafluorocyclopentene. In particular, potassium fluoride is suitable for use because of its low industrial cost. One of these alkali metal fluorides may be used individually, or two or more of these alkali metal fluorides may be used in combination. With regards to the form of the alkali metal fluoride, a powdered form that has been dried as thoroughly as possible is preferable from a viewpoint of reactivity, and a spray dried product is more preferable. A spray dried product of an alkali metal fluoride tends to have a large specific surface area and has excellent dispersibility compared to an alkali metal fluoride of a typical commercially available product that has not undergone spray drying.

The amount of the alkali metal fluoride that is used is preferably within a range of 1.0 molar equivalents to 2.0 molar equivalents, and more preferably within a range of 1.1 molar equivalents to 1.5 molar equivalents relative to 1-chloroheptafluorocyclopentene used as a feedstock. When the amount of the alkali metal fluoride that is used is not less than any of the lower limits set forth above, it is possible to sufficiently inhibit unreacted 1-chloroheptafluorocyclopentene from remaining in the fluorination step and further improve the yield of octafluorocyclopentene. Moreover, when the amount of the alkali metal fluoride that is used is not more than any of the upper limits set forth above, it is possible to prevent the amount of solid content inside the reactor after the fluorination reaction becoming excessively large and facilitate discharge of solid content from the inside of the reactor.

The following describes an example of various steps that may be included in the presently disclosed manufacturing method. An example of a manufacturing apparatus that can suitably implement the presently disclosed manufacturing method is an apparatus that includes a rectification column installed at the top of a reactor equipped with a stirrer and a feedstock supply pump. A receiver for trapping octafluorocyclopentene obtained as a reaction product may be installed at a withdrawal port of the rectification column. Moreover, a condenser for performing refluxing may be installed at the top of the rectification column and a coolant having a temperature within a range of −20° C. to 0° C. may be circulated. The manufacturing apparatus may include a feedstock tank that is in communication with the reactor via the feedstock supply pump and that is positioned such as to enable heating thereof by a heating mechanism such as an oil bath or a heater. The following describes an example of the various steps for a case in which the presently disclosed manufacturing method is implemented by a manufacturing apparatus having the configuration described above.

<Preparation Step>

First, in a preparation step, an alkali metal fluoride and a polar aprotic solvent are charged into the reactor, the reactor is heated, and thus a suspension containing the alkali metal fluoride suspended in the polar aprotic solvent is prepared in the reactor, for example. The temperature of the suspension inside the reactor is preferably maintained at 115° C. or higher until the point at which supply of 1-chloroheptafluorocyclopentene as a feedstock commences. Also note that the temperature of the suspension at the point at which feedstock supply commences is preferably 130° C. or lower. Setting the temperature of the suspension at the point at which feedstock supply commences as not lower than the lower limit set forth above can promote a fluorination reaction in a subsequent fluorination step and can shorten the fluorination reaction time. Moreover, setting the temperature of the suspension at the point at which the feedstock commences as not higher than the upper limit set forth above can inhibit concentration of 1-chloroheptafluorocyclopentene (feedstock) at the top of the rectification column installed at the top of the reactor, which is due to 1-chloroheptafluorocyclopentene having a low boiling point, and can improve the yield of octafluorocyclopentene.

<Feedstock Heating Step>

In a feedstock heating step, the 1-chloroheptafluorocyclopentene used as a feedstock is heated to not lower than 40° C. and not higher than 55° C. Hereinafter, the temperature of the feedstock that has been heated through the feedstock heating step is referred to as the "feedstock temperature". The feedstock temperature is preferably within a range of 45° C. to 55° C. When the feedstock temperature is not lower than the lower limit set forth above, it is possible to inhibit the temperature of the suspension decreasing and the rate of the fluorination reaction excessively decreasing due to the low boiling point (56° C.) of 1-chloroheptafluorocyclopentene used as the feedstock when this feedstock is supplied into the suspension in a fluorination step, and thus it is possible to improve fluorination reaction efficiency and also improve the yield of octafluorocyclopentene (reaction product). Moreover, when the feedstock temperature is not higher than the upper limit set forth above, gasification of 1-chloroheptafluorocyclopentene (feedstock) can be inhibited so as to enable supply thereof into the reactor at a stable rate by a transporting means such as a pump. The feedstock heating step commences prior to a feedstock supply step and continues until all of the required amount of feedstock is supplied.

<Feedstock Supply Step>

A feedstock supply step of transporting the feedstock into the reactor where a fluorination step is performed while heating the feedstock may optionally be implemented between the feedstock heating step and the fluorination step. In the feedstock supply step, the feedstock that has been heated to within the specific temperature range set forth above in the feedstock heating step is supplied into the suspension while being heated. The heating temperature in the feedstock supply step (hereinafter, also referred to as the "heating temperature during supply") is preferably equal to or higher than the feedstock temperature, and is more preferably at least 4° C. higher than the feedstock temperature. Moreover, the heating temperature during supply is normally 65° C. or lower, and preferably 60° C. or lower. Note that the "feedstock temperature" and the "heating temperature during supply" differ in terms that the "feedstock temperature" is the temperature of the feedstock itself, whereas the "heating temperature during supply" is the set temperature of a heating means, such as a heater, that is attached to feedstock supply piping or the like used in the feedstock supply step. By implementing the feedstock supply step that is accompanied by heating of the feedstock at a later stage than the feedstock heating step, the feedstock that has been heated to the feedstock temperature in the feedstock heating step can be supplied into the suspension without cooling. This can further improve fluorination efficiency in the fluorination step, which is the next step.

<Fluorination Step Through to Recovery Step>

In the fluorination step, the suspension inside the reactor that is obtained in the preparation step is maintained at 85° C. or higher while heated 1-chloroheptafluorocyclopentene is supplied into the suspension and is fluorinated to obtain octafluorocyclopentene. In the presently disclosed manufacturing method, reduction of the temperature of the suspension in the fluorination step due to the low boiling point of 1-chloroheptafluorocyclopentene can be effectively inhibited as a result of the suspension being maintained at 85° C. or higher in this step in addition to the previously described feedstock heating step being performed. Moreover, fluorination of 1-chloroheptafluorocyclopentene can be promoted as a result of the suspension being maintained at a temperature of 85° C. or higher in the fluorination step. This can inhibit recovery of unreacted 1-chloroheptafluorocyclopentene together with octafluorocyclopentene obtained as a reaction product and can improve the yield of octafluorocyclopentene.

More specifically, in the fluorination step, the 1-chloroheptafluorocyclopentene used as a feedstock is first supplied into the reactor using a pump or the like. The supply rate of 1-chloroheptafluorocyclopentene is preferably within a range of 0.4 g/min to 0.7 g/min. When the supply rate is not less than the lower limit set forth above, the time required for the fluorination step can be shortened, and the manufacturing efficiency of octafluorocyclopentene can be further improved. Moreover, when the supply rate is not more than the upper limit set forth above, reduction of the temperature inside the reactor caused by addition of 1-chloroheptafluorocyclopentene can be effectively inhibited, and reduction of the rate of the fluorination reaction in the fluorination step can be effectively inhibited. This enables further improvement of the yield of octafluorocyclopentene.

After the supply of 1-chloroheptafluorocyclopentene as a feedstock has commenced, withdrawal of product and trapping thereof in a cooled receiver is commenced approximately 30 minutes or more after the temperature at the top of the rectification column reaches 26° C. to 27° C. (recovery step). In this manner, octafluorocyclopentene that has been purified in the fluorination step can be recovered in the recovery step. During a period from when product withdrawal commences until the reaction time in the fluorination step elapses, withdrawal of product is continued, and the heating temperature of the reactor may be gradually increased depending on the temperature at the top of the rectification column and the state of refluxing. In this manner, the fluorination step and the recovery step may proceed concurrently from a point at which a certain time has elapsed after the start of the fluorination step.

The reaction time (required time) in the fluorination step depends on the size of the reactor and the scale on which the reaction is implemented, but is preferably 6 hours to 30 hours, and more preferably 7 hours to 15 hours. A reaction time that is too short leads to a poor conversion rate of 1-chloroheptafluorocyclopentene feedstock and reduced yield of octafluorocyclopentene, whereas a reaction time that is too long results in superfluous energy cost.

<Purification Step>

A purification step may optionally be implemented after the recovery step. In the purification step, the octafluorocyclopentene trapped in the receiver is subjected to a purification process such as distillation purification. In this manner, the purity of the product obtained in the fluorination step can be further increased.

EXAMPLES

The present disclosure is described in more detail below through examples. However, the scope of the present disclosure is not limited by the following examples. Note that pressures refer to gauge pressures. Moreover, the volume of solvent charged in a preparation step of each example or comparative example is the volume measured at 23° C. Furthermore, the yield of octafluorocyclopentene obtained in each example or comparative example was calculated as a ratio of the absolute yield of octafluorocyclopentene, as measured by gas chromatography analysis under the conditions shown below, relative to the additive amount of 1-chloroheptafluorocyclopentene as a feedstock.

<Gas Chromatography Analysis>

Gas chromatography analysis (GC analysis) was performed under the conditions shown below with respect to the reaction product obtained in each example or comparative example so as to analyze the content of octafluorocyclopentene in the reaction product.

Apparatus: HP-6890 (produced by Agilent Technologies, Inc.)

Column: Inert Cap-1 produced by GL Sciences Inc.; length: 60 m; internal diameter: 0.25 mm; film thickness: 1.5 μm Column temperature: Held at 40° C. for 10 minutes, subsequently raised at 20° C./min, and then held at 240° C. for 10 minutes Injection temperature: 200° C.

Carrier gas: Nitrogen

Split ratio: 100/1

Detector: Flame ionization detector (FID)

Example 1

<Preparation Step>

A glass reactor of 500 mL in capacity that was equipped with a stirrer, a rectification column (produced by Toka Seiki Co., Ltd.; column length: 30 cm; packing: Heli Pack No. 1), and a feeding pump (QT-150 produced by Yamazen) was charged with spray dried potassium fluoride (33.9 g) as an alkali metal fluoride and 150 mL of dry N,N-dimethylformamide as a polar aprotic solvent. The reactor was immersed in an oil bath, was heated to 120° C., and the contents thereof were stirred to obtain a suspension. The temperature of the suspension inside the reactor and the temperature at the top of the rectification column were each monitored by a thermocouple installed in a manner such as to enable measurement of the temperature of the suspension or the temperature at the top of the rectification column. A −10° C. coolant was circulated in a condenser of the rectification column.

<Feedstock Heating Step Through to Feedstock Supply Step>

Meanwhile, a stainless steel vessel equipped with a valve was charged with 1-chloroheptafluorocyclopentene as a feedstock, was immersed in an oil bath, and was heated such that the feedstock inside the vessel reached a temperature of 45° C. (feedstock temperature). A tube cover heater was wrapped around tubing connected to the stainless steel vessel containing the feedstock, a pump, and the reactor, and was used to heat the tubing to 50° C. (heating temperature during supply).

<Fluorination Step Through to Recovery Step>

Once the temperature of the suspension inside the reactor reached 117° C., supply of 1-chloroheptafluorocyclopentene into the reactor as a feedstock was commenced. The initial feedstock supply rate was set as 0.62 g/min and the supply rate was finely adjusted during the feedstock supply period while supplying the feedstock over 2.9 hours. The total supplied amount of feedstock was 114.9 g. During this period, the minimum temperature of the suspension inside the reactor was 93.1° C. After approximately 1.2 hours from the start of feedstock feeding, product withdrawal was commenced with a reflux ratio of 60 (temperature at top of rectification column: 26.5° C.). Thereafter, heating at 120° C. and product withdrawal with a reflux ratio of 60 were continued, and the oil bath temperature was raised in stages to 130° C. and 140° C. while observing the temperature at the top of the rectification column and the state of refluxing. The temperature at the top of the rectification column started to decrease after 7.7 hours from the start of feedstock supply. Therefore, the temperature of the oil bath was lowered to 120° C., an aspirator was connected to a distillation head of the rectification column, and the system was depressurized by a pressure of −0.09 MPa so as to recover holdup. The total amount of crude product that was recovered was 100.8 g. The content of octafluorocyclopentene (target product) in the crude product was determined from the results of gas chromatography analysis. Moreover, a ratio of the absolute yield of the obtained target product relative to the supplied amount of feedstock was calculated. The results are shown in Table 1.

Example 2

The feedstock temperature in the feedstock heating step was changed to 55° C. and the heating temperature during supply in the feedstock supply step was changed to 60° C. Moreover, with the exception that the feedstock supply time, the total supplied amount, the start time of the recovery step, and the reaction time of the fluorination step were changed as shown in Table 1, operations were carried out in the same way as in Example 1. Note that the temperature of the suspension at the point at which feedstock supply commenced, the minimum temperature of the suspension in the fluorination step, and the temperature at the top of the rectification column at the point at which the recovery step commenced were as shown in Table 1. Moreover, the total amount of crude product recovered through the recovery step was 102.0 g. The result for the yield of target product calculated in the same way as in Example 1 is shown in Table 1.

Example 3

The feedstock temperature in the feedstock heating step was changed to 45° C. and the heating temperature during supply in the feedstock supply step was changed to 55° C. Moreover, with the exception that the feedstock supply time, the total supplied amount, the start time of the recovery step, and the reaction time of the fluorination step were changed as shown in Table 1, operations were carried out in the same way as in Example 1. Note that the temperature of the suspension at the point at which feedstock supply commenced, the minimum temperature of the suspension in the fluorination step, and the temperature at the top of the rectification column at the point at which the recovery step commenced were as shown in Table 1. Moreover, the total amount of crude product recovered through the recovery step was 101.4 g. The result for the yield of target product calculated in the same way as in Example 1 is shown in Table 1.

Comparative Example 1

Operations were carried out in the same way as in Example 1 with the exception that the feedstock heating step was not performed and heating was not performed in the feedstock supply step. Note that the temperature of the suspension at the point at which feedstock supply commenced, the total supplied amount of feedstock, and the minimum temperature of the suspension in the fluorination step were as shown in Table 1. After approximately 2 hours from the start of product withdrawal, the temperature at the top of the rectification column increased to 30.7° C., and it was necessary to temporarily suspend product withdrawal. The total amount of crude product recovered through the recovery step was 101.4 g. The result for the yield of target product calculated in the same way as in Example 1 is shown in Table 1. In Table 1, "KF" indicates potassium fluoride and "DMF" indicates N,N-dimethylformamide.

TABLE 1

|  |  |  |  | Example 1 | Example 2 | Example 3 | Comparative Example 1 |
|---|---|---|---|---|---|---|---|
| Feedstock heating step | Feedstock | 1-Chloroheptafluorocyclopentene (g) | | 114.9 | 114.4 | 114.6 | 114.3 |
|  |  | Feedstock temperature (° C.) | | 45 | 55 | 45 | 23 |
| Feedstock supply step | Heating temperature during supply (° C.) | | | 50 | 60 | 55 | 22 |
|  | Supply time (hr) | | | 2.9 | 3.18 | 3.0 | 2.2 |
| Fluorination step | Fluorinating agent | Alkali metal fluoride | Type | KF | KF | KF | KF |
|  |  |  | Amount (molar equivalents; feedstock basis) | 1.16 | 1.16 | 1.16 | 1.16 |
|  | Solvent | Polar aprotic solvent | Type | DMF | DMF | DMF | DMF |
|  |  |  | Amount (mL) | 150 | 150 | 150 | 150 |
|  |  |  | Ratio (mL/g; feedstock basis) | 1.31 | 1.31 | 1.31 | 1.31 |
|  | Suspension | Temperature at point at which feedstock supply commences (° C.) | | 117.0 | 117.0 | 116.0 | 115.2 |
|  |  | Minimum temperature (° C.) | | 93.1 | 94.3 | 92.4 | 82.6 |
|  | Reaction time (hr) | | | 7.7 | 6.0 | 7.5 | — |
| Recovery step | Start time (point after start of fluorination step [hr]) | | | 1.2 | 1.6 | 1.7 | 1.2 |
|  | Initial temperature at top of rectification column (° C.) | | | 26.5 | 26.0 | 26.0 | 26.5 |
| Evaluation | Yield (%) | | | 94.3 | 93.3 | 90.4 | 79.1 |

It can be seen from Table 1 that it was possible to sufficiently increase the yield of octafluorocyclopentene in Examples 1 to 3 in which a feedstock heating step of heating a feedstock to not lower than 40° C. and not higher than 55° C. and a fluorination step of maintaining a suspension containing a polar aprotic solvent and an alkali metal fluoride at 85° C. or higher while supplying the heated feedstock into the suspension and performing fluorination thereof to obtain octafluorocyclopentene were implemented.

On the other hand, it can be seen that the yield could not be sufficiently increased in Comparative Example 1 in which a feedstock heating step of heating a feedstock to not lower than 40° C. and not higher than 55° C. was not implemented.

INDUSTRIAL APPLICABILITY

According to the present disclosure, it is possible to provide a manufacturing method that can sufficiently increase the yield of octafluorocyclopentene.

The invention claimed is:

1. A method of manufacturing octafluorocyclopentene by bringing 1-chloroheptafluorocyclopentene into contact with an alkali metal fluoride, comprising:
    a feedstock heating step of heating 1-chloroheptafluorocyclopentene to not lower than 40° C. and not higher than 55° C.;
    a fluorination step of maintaining a suspension containing a polar aprotic solvent and the alkali metal fluoride at 85° C. or higher while supplying heated 1-chloroheptafluoropentene into the suspension and performing fluorination thereof to obtain octafluorocyclopentene; and
    a recovery step of recovering the octafluorocyclopentene that is produced in the fluorination step.

2. The method of manufacturing octafluorocyclopentene according to claim 1, wherein the polar aprotic solvent is N,N-dimethylformamide or N,N-dimethylacetamide.

3. The method of manufacturing octafluorocyclopentene according to claim 1, wherein the alkali metal fluoride is potassium fluoride or cesium fluoride.

\* \* \* \* \*